(12) United States Patent
Senn et al.

(10) Patent No.: US 6,753,296 B1
(45) Date of Patent: Jun. 22, 2004

(54) METHOD FOR IMPROVING PLANT GROWTH

(75) Inventors: Robert Senn, Witterswil (CH); Dieter Hofer, Liestal (CH); Thomas Thieme, Sagerheide (DE); Larry Zang, Highpoint, NC (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/110,452

(22) PCT Filed: Oct. 11, 2000

(86) PCT No.: PCT/EP00/10024

§ 371 (c)(1),
(2), (4) Date: Apr. 10, 2002

(87) PCT Pub. No.: WO01/26468

PCT Pub. Date: Apr. 19, 2001

(51) Int. Cl.[7] .................... A01N 43/08; A01N 43/40; A01N 43/78; A01N 43/88

(52) U.S. Cl. .................. 504/221; 504/222; 504/223; 504/230; 504/231; 504/244; 504/266; 504/294

(58) Field of Search ................. 504/221, 222, 504/230, 231, 223, 244, 266, 294

(56) References Cited

U.S. PATENT DOCUMENTS

| | | | | |
|---|---|---|---|---|
| 5,876,739 A | | 3/1999 | Turnblad et al. ............ | 424/408 |
| 5,883,045 A | * | 3/1999 | Wada et al. ................ | 504/116 |
| 6,164,012 A | * | 12/2000 | Lechelt-Kunze et al. .... | 47/57.6 |
| 6,261,996 B1 | * | 7/2001 | Klittich et al. ............. | 504/100 |

FOREIGN PATENT DOCUMENTS

EP 0 113 070 A 7/1984

OTHER PUBLICATIONS

Palumbo, J.C. et al., Hortscience, American Society of Horticultural Science, vol. 30, No. 5, Aug., 1995, pp. 997–999.

S.J. Fleischer, M.D. Orzolek, D. DeMackiewicz & L. Otjen, J. Econ. Entomol., vol. 91, No. 4, 1998, pp. 940–944.

J.C. Palumbo, D.L. Kerns, C.E. Engle, C.A. Sanchez & M. Wilcox, J. Econ. Entomol., vol. 89, No. 3, 1996, pp. 738 and 741.

K.S. Pike, G.L. Reed, G.T. Graf & D. Allison, Great Plains Agric. Council Publ.: Proc. Of 5th Russian Wheat Aphid Conference, Jan. 26–28, 1992, No. 142, 1992.

* cited by examiner

*Primary Examiner*—S. Mark Clardy
(74) *Attorney, Agent, or Firm*—Rose M. Allen

(57) ABSTRACT

Disclosed is a method of improving the growth of plants wherein at least one compound of formula (I)

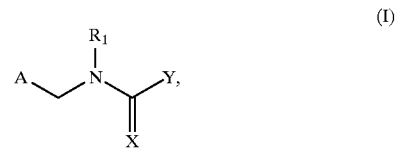

wherein

A is 2-chloropyrid-5-yl, 2-methylpyrid-5-yl, 1-oxido-3-pyridinio, 2-chloro-1-oxido-5-pyridinio, 2,3-dichloro-1-oxido-5-pyridinio, tetrahydrofuran-3-yl, 5-methyl-tetrahydrofuran-3-yl or 2-chlorothiazol-5-yl group, R is hydrogen, $C_1$–$C_6$alkyl, phenyl-$C_1$–$C_4$alkyl, $C_3$–$C_6$cycloalkyl, $C_2$–$C_6$alkenyl or $C_2$–$C_6$alkynyl;

Y is —N(R)($R_2$) or $SR_2$;

$R_1$ and $R_2$ are independently of each other $C_1$–$C_4$-alkyl, $C_1$–$C_4$-alkenyl, $C_1$–$C_4$-alkinyl, —C(=O)—$CH_3$ or benzyl; or together form a group —$CH_2$—$CH_2$—, —$CH_2$—$CH_2$—$CH_2$—, —$CH_2$—O—$CH_2$—, —$CH_2$—S—$CH_2$—, —$CH_2$—NH—$CH_2$— or —$CH_2$—N($CH_3$)—$CH_2$—; and X is N—$NO_2$ or N—CN or CH—$NO_2$; or, where appropriate, a tautomer thereof, in each case in free from or in salt form; is applied to the plant or the locus thereof.

8 Claims, No Drawings

METHOD FOR IMPROVING PLANT GROWTH

FIELD OF THE INVENTION

The present invention relates to a method of improving the growth of plants comprising applying to the plants or the locus thereof at least one compound selected from the class of the neonicotinoids.

BACKGROUND OF THE INVENTION

Certain methods of improving plant growth are described in the literature. These methods are usually based on conventional fertilizing. The biological effects of those known methods are however not entirely satisfactory in the area of agriculture. There is therefore still a need to improve the growth of the plants basically for obtaining higher crop yields, as well as the reduction of the use of fertilizers needed.

SUMMARY OF THE INVENTION

The present invention provides a new method of improving plant growth, more specifically, a method for improving plant growth of crops such as canola (rape) seed, eggplants, rice, potatoes and soybeans, wherein at least one neonicotinoid compound is applied to the plant or the locus thereof.

DESCRIPTION OF SPECIFIC EMBODIMENTS

Preferred is a method of improving the growth of plants wherein at least one neonicotinoid compound of formula (I)

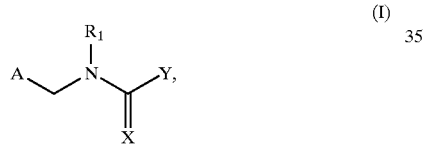

(I)

wherein

A is 2-chloropyrid-5-yl, 2-methylpyrid-5-yl, 1-oxido-3-pyridinio, 2-chloro-1-oxido-5-pyridinio, 2,3-dichloro-1-oxido-5-pyridinio, tetrahydrofuran-3-yl, 5-methyl-tetrahydrofuran-3-yl or 2-chlorothiazol-5-yl group, R is hydrogen, $C_1$–$C_6$alkyl, phenyl-$C_1$–$C_4$alkyl, $C_3$–$C_6$cycloalkyl, $C_2$–$C_6$alkenyl or $C_2$–$C_6$alkynyl;

Y is —N(R)($R_2$) or $SR_2$;

$R_1$ and $R_2$ are independently of each other $C_1$–$C_4$-alkyl, $C_1$–$C_4$-alkenyl, $C_1$–$C_4$-alkinyl, —C(=O)—$CH_3$ or benzyl; or together form a group —$CH_2$—$CH_2$—, —$CH_2$—$CH_2$—$CH_2$—, —$CH_2$—O—$CH_2$—, —$CH_2$—S—$CH_2$—, —$CH_2$—NH—$CH_2$— or —$CH_2$—N($CH_3$)—$CH_2$—; and X is N—$NO_2$ or N—CN or CH—$NO_2$; or, where appropriate, a tautomer thereof, in each case in free from or in salt form, is applied to the plant or the locus thereof.

The compounds (I) may be in the form of tautomers. Accordingly, hereinbefore and hereinafter, where appropriate the compound compounds (I) are to be understood to include corresponding tautomers, even if the latter are not specifically mentioned in each case.

The compounds of the formula (I) are capable of forming acid addition salts. Those salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halo-substituted, $C_1$–$C_4$alkanecarboxylic acids, for example acetic acid, saturated or unsaturated dicarboxylic acids, for example oxalic, malonic, succinic, maleic, fumaric or phthalic acid, hydroxycarboxylic acids, for example ascorbic, lactic, malic, tartaric or citric acid, or benzoic acid, or with organic sulfonic acids, such as unsubstituted or substituted, for example halo-substituted, $C_1$–$C_4$alkane- or aryl-sulfonic acids, for example methane- or p-toluenesulfonic acid. Furthermore, compounds of formula (I) having at least one acidic group are capable of forming salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propylamine, or a mono-, di- or tri-hydroxy-lower alkylamine, for example mono-, di- or tri-ethanolamine, In addition, corresponding internal salts may also be formed. Preference is given within the scope of the invention to agrochemically advantageous salts. In view of the close relationship between the compounds of formula (I) in free form and in the form of their salts, any reference hereinbefore or hereinafter to the free compounds of formula (I) or to their respective salts is to be understood as including also the corresponding salts or the free compounds of formula (I), where appropriate and expedient. The same applies in the case of tautomers of compounds of formula (I) and the salts thereof. The free form is generally preferred in each case.

Preferred compounds of the formula (I) are those wherein

A is a pyrid-3-yl, 2-chloropyrid-5-yl, 2-chloro-1-oxido-5-pyridinio or 2-chlorothiazol-5-yl group; particularly a 2-chloropyrid-5-yl group or preferably a 2-chlorothiazol-5-yl group;

wherein R is $C_1$–$C_6$alkyl, phenyl-$C_1$–$C_4$alkyl, $C_3$–$C_4$alkenyl or $C_3$–$C_4$alkynyl;

more especially $C_1$–$C_4$alkyl, preferably methyl;

$R_1$ and $R_2$ are independently of each other $C_1$–$C_4$-alkyl or benzyl, or together a group —$CH_2$—$CH_2$—, —$CH_2$—$CH_2$—$CH_2$—, —$CH_2$—O—$CH_2$—, —$CH_2$—S—$CH_2$—, —$CH_2$NH—$CH_2$—, —$CH_2$—N($CH_3$)—$CH_2$—, especially group —$CH_2$—$CH_2$— or —$CH_2$—O—$CH_2$—, particularly —$CH_2$—$CH_2$—; and X is N—$NO_2$ or N—CN, more especially N—$NO_2$.

Especially preferred is a method of improving the growth of plants comprising the application to the plant or the locus thereof of an effective amount of a compound selected from the group consisting of: a compound of the formula

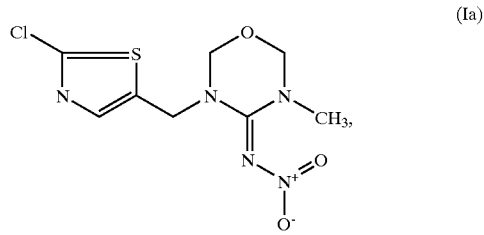

(Ia)

imidacloprid, clothianidin (TI-435), nitenpyram, thiacloprid, acetamiprid and MTI-446; particularly the compound of the formula (Ia) (thiarnethoxam).

The compound of the formula (Ia) is known for instance from EP-A-5805 53;

Imidacloprid is known from The Pesticide Manual, 11th Ed. (1997), The British Crop Protection Council, London, page 706;

Nitenpyram from The Pesticide Manual, 11th Ed. (1997), The British Crop Protection Council, London, page 880;

TI-435 from EP-A-376,279;

MTI-446 from EP-A-649,845; and

Thiacloprid from EP-A-235,725.

Surprisingly, it has been found that the application of the compounds of the formula (I) to the plants or the locus thereof results in a quite unexpectedly enhanced plant growth. It has now been found, that the action of the compounds of the formula (I) goes far beyond their well-known pesticidal action. It has been shown, that the compounds of the formula (I) exhibit an action termed plant growth in the frame of the instant invention. Under the term plant growth there are understood various sorts of improvements of plants which are not connected to the control of pests with the said compound (I). For example such advantageous properties that may be mentioned are improved crop characteristics including: emergence, crop yields, protein content, more developed root system, tillering increase, increase in plant height, bigger leaf blade, less dead basal leaves, stronger tillers, greener leaf color, less fertilizers needed, less seeds needed, more productive tillers, earlier flowering, early grain maturity, less plant verse (lodging), increased shoot growth, improved plant vigor, and early germination; or any other advantages familiar to a person skilled in the art.

Especially preferred is the use of the said neonicotiniod compounds in a method for the improvement of the growth plants which are essentially free of insects and representatives of the order Acarina.

It has been shown, that compounds of the instant formula (I) have a good effect on the plant growth. As a rule, a good effect means at least 10% earlier emergence, crop yields, more developed root system, increase in plant height, bigger leaf blade, less fertilizers needed, less seeds needed increased shoot growth, improved plant vigor etc.

A further aspect of the invention is a method of using a neonicotinoid compound in a method for Improving the growth of plants.

A further aspect of the invention is the use of a neonicotinoid compound in a method for improving the growth of plants.

Still a further aspect of the invention is a method of using a composition comprising a neonicotinoid compound in a method for improving the growth of plants. Crops which can be improved according to the present method include cereals, such as wheat, barley, rye, oats, rice, maize and sorghum; beet, such as sugar beet and fodder beet; fruit, for example pomes, stone fruit and soft fruit, such as apples, pears, plums, peaches, almonds, cherries and berries, e.g. strawberries, raspberries and blackberries; leguminous fruits, such as beans, lentils, peas and soybeans; oil plants, such as rape, mustard, poppy, olives, sunflowers, coconut, castor oil plants, cocoa beans and groundnuts; cucurbitaceae, such as marrows, cucumbersand melons; fibre plants, such as cotton, flax, hemp and jute; citrus fruit, such as oranges, lemons, grapefruit and mandarins; vegetables, such as spinach, lettuce, asparagus, cabbages, carrots, onions, tomatoes, potatoes and paprika; lauraceae, such as avocados, cinnamon and camphor; and also tobacco, nuts, coffee, aubergines, sugar cane, tea, pepper, vines, hops, bananas, natural rubber plants and ornamentals; especially rice, beans, soybeans, rape and potatoes.

The invention accordingly relates also to compositions comprising the compounds of the formula (I) and the use of the said compositions, such as emulsifiable concentrates, suspension concentrates, directly sprayable or dilutable solutions, coatable pastes, dilute emulsions, wettable powders, soluble powders, dispersible powders, wettable powders, dusts, granules or encapsulations in polymeric substances, which comprise at least one of the compounds according to the invention, the type of formulation being chosen in accordance with the intended objectives and the prevailing circumstances.

The compounds of the formula (I) are used in those compositions in pure form, a solid the compounds of the formula (I) being used, for example, in a specific particle size, or, preferably, together with at least one of the adjuvants customary in formulation technology, such as extenders, e.g. solvents or solid carriers, or surface-active compounds (surfactants).

Suitable formulation adjuvants are, for example, solid carriers, solvents, stabilisers, slow-release adjuvants, dyes and optionally surface-active substances (surfactants). Suitable carriers and adjuvants in this case include all substances customarily used in crop protection products, especially in products for controlling snails and slugs. Suitable adjuvants, such as solvents, solid carriers, surface-active compounds, non-ionic surfactants, cationic surfactants, anionic surfactants and further adjuvants in the compositions used in accordance with the invention are, for example, the same as those described in EP-A-736 252; are fully incorporated by reference herein for their disclosure relating to useful formulation adjuvants.

The compositions usually contain from 0.1 to 99%, especially from 0.1 to 95%, of a compound of the formula (I) and from 1 to 99.9%, especially from 5 to 99.9%, of at least one solid or liquid adjuvant, it generally being possible for from 0 to 25%, especially from 0.1 to 20%, of the composition to be surfactants (in each case percentages are by weight). Whereas commercial products will preferably be formulated as concentrates, the end user will normally employ dilute formulations which have considerably lower concentrations of one or more compounds of the formula (I). Preferred formulations have especially the following composition (%=percent by weight):

Emulsifiable concentrates:

| | |
|---|---|
| Compound of the formula (I): | 1 to 95%, preferably 5 to 20% |
| surfactant: | 1 to 30%, preferably 10 to 20% |
| solvent: | 5 to 98%, preferably 70 to 85% |

Dusts:

| | |
|---|---|
| Compound of the formula (I): | 0.1 to 10%, preferably 0.1 to 1% |
| Solid carrier: | 99.9 to 90%, preferably 99.9 to 99% |

Suspension concentrates:

| | |
|---|---|
| Compound of the formula (I): | 5 to 75%, preferably 10 to 50% |
| water: | 94 to 24%, preferably 88 to 30% |
| surfactant: | 1 to 40%, preferably 2 to 30% |

Wettable powders:

| | |
|---|---|
| Compound of the formula (I): | 0.5 to 90%, preferably 1 to 80% |
| surfactant: | 0.5 to 20%, preferably 1 to 15% |
| solid carrier: | 5 to 99%, preferably 15 to 98% |

Granules:

| | |
|---|---|
| Compound of the formula (I): | 0.5 to 30%, preferably 3 to 15% |
| solid carrier: | 99.5 to 70%, preferabty 97 to 85% |

The compositions according to the invention are prepared in known manner: in the absence of adjuvants, for example, by grinding, sieving and/or compressing a solid compound of the formula (I), for example to a specific particle size, and, in the presence of at least one adjuvant, for example, by intimately mixing and/or grinding the compound of the formula (I) with the adjuvant(s). The invention relates also to those methods of preparing the compositions according to the invention and to the use of compounds I in the preparation of such compositions.

The invention relates also to the methods of applying the compositions of the type mentioned, such as spraying, atomising, dusting, coating, dressing, scattering or pouring, which are chosen in accordance with the intended objectives and the prevailing circumstances, and to the use of the compositions for the improvement of the plants of the type mentioned. Typical rates of concentration are from 0.1 to 1000 ppm, preferably from 0.1 to 500 ppm, of compound of the formula (I). The rates of application per hectare are generally from 1 to 2000 g of compound of the formula (I) per hectare, especially from 1 to 1000 g/ha, preferably from 5 to 600 g/ha.

A preferred method of application is application to the leaves of the plants (foliar application), the frequency and rate of application depending on the desired improvement of the crop plant in question. The compound of the formula (I) may, however, also penetrate the plants through the root system (systemic action) as a result of impregnation of the locus of the plant with a liquid formulation or by incorporation of the compound of the formula (I) in solid form, for example in the form of granules, in the locus of the plant, for example in the soil (soil application). In the case of paddy rice crops, such granules may be applied in metered amounts to the flooded rice field.

In one embodiment, commercial products will preferably be formulated as concentrates whereas the end user will normally use dilute formulations.

The compositions according to the invention are also suitable for the treatment of plant propagation material, including genetically modified propagation material, e.g. seed, such as fruit, tubers or grains, or plant cuttings, The propagation material may be treated with the composition before planting, for example seed may be dressed before sowing. The compounds according to the invention may also be applied to seed grains (coating) either by impregnating the grains with a liquid formulation or by coating them with a solid formulation. The composition may also be applied to the planting site when the propagation material is being planted, for example may be applied to the seed furrow during sowing. The invention relates also to that method of treating plant propagation material and to the plant propagation material so treated.

The compounds of formula (I) are normally applied to plant propagation material in the form of compositions, but also can be applied to the seed or lo the locus of propagation thereof (such as a furrow), simultaneously or in succession, with further compounds. These further compounds can be fertilizers or micronutrient donors or other preparations that influence plant growth. They can also be selective pesticides or mixtures of several of these preparations, if desired together with further carriers, surfactants or application-promoting adjuvants customarily employed in the art of formulation.

In connection with the treatment of plant propagation material, favorable rates of application are in general 0.0005 to not more than 1 kg, in particular 0.01–0.8 kg, more particularly 0.1–0.5 kg of one or more compounds of the formula (I) per 100 kg of material to be protected. However, the application conditions depend essentially on the nature (surface area, consistency, moisture content) of the material and on its environmental factors. Accordingly, within these ranges, those skilled in the art will choose, on the basis of their general body of knowledge and, where appropriate, a few experiments, doses which are non-phytotoxic but effective for improving the plant growth.

The techniques of seed treatment application are well known to those skilled in the art, and they may be used readily in the context of the present invention. The compounds of the formula (I) can be formulated and applied as a slurry, a solid seed coating, a soak, or as a dust on the surface of the seed. There also may be mentioned, e.g., film-coating or encapsulation. The coating processes are well known in the art, and employ, for seeds, the techniques of film-coating or encapsulation, or for the other multiplication products, the techniques of immersion. Needless to say, the method of application of the compounds to the seed may be varied and the invention is intended to include any technique which is to be used.

A preferred method of applying the mixture to the plant propagation material according to the invention consists in spraying or wetting the plant propagation material with a liquid preparation, or mixing the plant material with a solid preparation of the compounds of the formula (I).

The compounds of this invention may be formulated or mixed in the seed treater tank or combined on the seed by overcoating with other seed treating agents. The agents to be mixed with the compounds of this invention may be for the control of pests, or further modification of growth, nutrition, or for the control of plant diseases.

Formulation Examples
(%=Per Cent by Weight)

The examples which follow are intended to illustrate and not limit the invention, "compound of the formula (I)" being understood as meaning one or several of the compounds of the formula (I).

EXAMPLE F1

Emulsifiable concentrates

|  | a) | b) | c) |
|---|---|---|---|
| Compound of the formula (I) | 25% | 40% | 50% |
| calcium dodecylbenzenesulfonate | 5% | 8% | 6% |
| castor oil polyethylene glycol ether | 5% | — | — |
| Tributylphenol polyethylene glycol ether | — | 12% | 4% |
| Cyclohexanone | — | 15% | 20% |
| xylene mixture | 65% | 25% | 20% |

Emulsions of any desired concentration can be prepared from this concentrate by dilution with water, and can be employed in crop protection and in seed treatment applications.

EXAMPLE F2

Dusts

|  | a) | b) |
|---|---|---|
| Compound of the formula (I) | 5% | 8% |
| Talc | 95% | — |
| Kaolin | — | 92% |

Ready-to-use dusts are obtained by mixing the compounds of the formula (I) with the carrier and grinding the mixture in a suitable mill. Such powders can be used for dry-dressing seeds.

EXAMPLE F3

Wettable powders

|  | a) | b) | c) |
|---|---|---|---|
| Compound of the formula (I) | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether | — | 2% | — |
| highly dispersed silicic acid | 5% | 10% | 10% |
| kaolin | 62% | 27% | — |

The compound of the formula (I) is mixed thoroughly with the additives and the mixture is ground thoroughly in a suitable mill affording wettable powders which can be diluted with water to give suspensions of any desired concentration. Such slurries can be used for carrying out furrow treatments on prior to planting crops of plants and also for wet- or moist-dressing material which can be propagated, for example oil seeds or tubers of plants.

EXAMPLE F4

Suspoemulsions

|  | a) |
|---|---|
| Compound of the formula (I) | 22.5% |
| sulfated nonylphenol (polyoxyethylene condensate) | 0.1% |
| phosphated tristyrylphenol (polyoxyethylene condensate) |  |
| sodium lignosulfonate (polyoxyethylene condensate) | 2% |
| NaOH (50%) | 0.1% |
| silicone defoaming agent | 0.1% |
| pigment(s) | 9.5% |
| Glycerin | 20% |
| xanthan gum | 0.2% |
| Water | 41.5% |

This formulation is suitable for mixtures of solid and liquid compounds of the formula (I). The solid compounds of the formula (I) are mixed thoroughly with a portion of the emulsifiers and water and the mixture is ground thoroughly in a suitable mill. Another portion of the emulsifiers and water are mixed with the liquid compounds of the formula (I). The two mixtures are combined along with any other inert ingredients (such as pigments, thickeners, etc.) that are to be used in the formulation. Such suspoemulsions can be used for carrying out in furrow treatments prior to planting crops of plants and also for wet- or moist-dressing material which can be propagated, for example oil seeds or tubers of plants.

Biological Examples
(%=Per Cent by Weight Unless Otherwise Indicated)

The examples which follow are intended to illustrate and not limit the invention.

EXAMPLE B1

Emergence

Canola seed is treated with the composition of the invention containing Thiamethoxam, at a rate of 300 g Thiamethoxam per 100 kg seed, and is seeded following procedures which correspond to conditions found in practice. Untreated seeds from the same origin are used for comparison purposes. Emergence (plants per meter) is evaluated. In the case of treated seeds, about 20% more plants per meter emerge that in the case of untreated plants.

EXAMPLE B2/B3

Vigor of Rice (*Orvza sativa* L. cv. Nihonbare) and Eggplant (*Solanum melongena* L. cv. Marfa)

Plant are grown in a commercially available pathogen-free soil mixture. 2 weeks (eggplants 3 weeks) after planting seedlings are transplanted into 600 ml pots and drench treated with 10 mg Thiamethoxam in 20 ml water per pot. They were fertilised once or twice a week. Up to 10 weeks after treatment, fresh- and dry-weight of shoots and roots and numbers of leaves are determined. Protein content is measured by the method of Bradford (1976, Anal. Biochem., 72, 248–254) with BSA (bovine serum albumin) as standard: Homogenisation of leaf material in liquid $N_2$ in a mortar. Extraction in phosphate buffer (pH 7.5, 0.1M, 2/1 vol/weight). After centrifugation supematant is separated from pellet and stored at $-20°$ C. until protein determination. For comparison of treated and check, mg proteing/g fresh weight is calculated.

Tables B2 and B3: Differences between treated plants and Check given as factors (e.g. fresh weight of treated/Fresh weight of check). Factors >1 indicate an enhancement of vigor of treated plants. FW: fresh weight; DW: dry weight; Protein ((mg/g treated plant)/(mg/g check))

TABLE B2

Rice

| Week | Size | Shoot | | Root | | Protein |
| | | FW | DW | FW | DW | |
|---|---|---|---|---|---|---|
| 1 | 1.0 | 1.0 | 1.0 | 1.0 | 0.8 | 1.1 |
| 2 | 1.0 | 1.0 | 1.1 | 0.8 | 1.1 | 1.0 |
| 3 | 1.0 | 1.2 | 1.3 | 0.6 | 1.3 | 1.0 |
| 4 | 1.1 | 1.3 | 1.2 | 1.5 | 1.4 | 1.0 |
| 5 | 1.1 | 1.2 | 1.1 | 1.0 | 0.9 | 1.0 |
| 6 | 1.2 | 1.3 | 1.1 | 1.6 | 1.5 | 1.0 |
| 7 | 1.1 | 1.3 | 1.2 | 1.3 | 1.3 | 1.1 |
| 8 | 1.1 | 1.4 | 1.4 | 1.8 | 1.5 | 1.0 |
| 9 | 1.2 | 1.2 | 1.2 | 1.0 | 1.0 | 0.9 |
| 10 | 1.3 | 1.3 | 1.3 | 2.0 | 2.0 | 0.7 |

TABLE B3

Eggplant

| Week | Size | Shoot | | Root | | Leaf | Protein |
| | | FW | DW | FW | DW | No | |
|---|---|---|---|---|---|---|---|
| 1 | 1.0 | 0.9 | 0.9 | 1.0 | 1.0 |  | 1.0 |
| 2 | 1.1 | 0.7 | 1.1 | 1.2 | 1.2 |  | 1.1 |
| 3 | 1.1 | 1.2 | 1.1 | 1.1 | 1.1 |  | 1.0 |
| 4 | 1.0 | 1.1 | 1.1 | 1.0 | 1.0 |  | 1.6 |
| 5 | 1.0 | 1.0 | 1.1 | 0.9 | 1.0 | 1.1 | 1.0 |
| 6 | 1.3 | 1.3 | 1.3 | 0.9 | 0.9 | 1.3 | 1.1 |
| 7 | 1.2 | 1.1 | 1.1 | 0.8 | 0.7 | 1.3 | 1.4 |
| 8 | 1.2 | 0.7 | 0.9 | 0.6 | 0.6 | 1.2 | 1.4 |
| 9 | 1.4 | 0.7 | 1.1 | 0.9 | 1.1 | 1.6 | 2.5 |
| 10 | 1.4 | 1.1 | 1.1 | 1.1 | 1.3 | 1.4 | 1.3 |

Since the soil used does not contain pathogens and the biological activity can be assumed as low, the effects are caused by direct growth stimulation and not by side effects of Thiamethoxam against soil organisms.

EXAMPLE B4

Yield

Potato tubers are treated with the composition of the invention containing Imidacloprid, at a rate of 500 g Imidacloprid per 100 kg seed and are planted following procedures which correspond to conditions found in practice. The crop is harvested from the field at maturity. Untreated tubers from the same origin are used for comparison purposes. Crop yield is evaluated and found to be significantly higher in the case of treated potato tubers than with untreated tubers.

In summary, it is seen that this invention provides a new method for improving the plant growth. Variations may be made in proportions, procedures and materials without departing from the scope of the invention as defined by the following claims.

We claim:
1. A method of improving the growth of a plant which is essentially free of insects, characterized in that a plant-growth-improving amount of at least one plant-growth-improving compound of the formula:

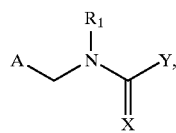

(I)

in which:
A is a 2-chloropyrid-5-yl, 2-methylpyrid-5-yl, 1-oxido-3-pyridinio, 2-chloro-1-oxido-5-pyridinio, 2,3-dichloro-1-oxido-5-pyridinio, tetrahydrofur-3-yl, 5-methyl-tetrahydrofur-3-yl or 2-chlorothiazol-5-yl group, R is hydrogen, $C_1$–$C_6$alkyl, phenyl-$C_1$–$C_4$alkyl, $C_3$–$C_6$cycloalkyl, $C_2$–$C_6$alkenyl or $C_2$–$C_6$alkynyl; is —N(R)(R$_2$) or —SR$_2$;

R$_1$ and R$_2$ are either, independently of each other, $C_1$–$C_4$alkyl, $C_2$–$C_4$alkenyl, $C_2$–$C_4$alkinyl, —C(=O)—CH$_3$ or benzyl; or taken together, form a group —CH$_2$—CH$_2$—, —CH$_2$—CH$_2$—CH$_2$—, —CH$_2$—O—CH$_2$—, —CH$_2$—S—CH$_2$—, —CH$_2$—NH—CH$_2$ or —CH$_2$—N(CH$_3$)—CH$_2$—; and X is N—NO$_2$ or N—CN or CH—NO$_2$;

or in which A is 2-chloropyrid-5-yl, X is N—CN, Y is CH$_3$ and R$_1$ is methyl;

or in which A is 2-chlorothiazol-5-yl, X is N—NO$_2$, Y is —N(R)(R$_2$), R is hydrogen, R$_1$ is hydrogen and R$_2$ is methyl;

or in which A is tetrahydrofur-3-yl, X is N—NO$_2$, Y is —N(R)(R$_2$), R is hydrogen, R$_1$ is hydrogen and R$_2$ is methyl;

or, where appropriate, a tautomer thereof, in each case in free from or in salt form, is applied to the plant or the locus thereof.

2. A method according to claim 1, characterized in that the compound of the formula (I) is thiamethoxam.

3. A method according to claim 1, characterized in that the compound of the formula (I) is imidacloprid.

4. A method according to claim 1, characterized in that the compound of the formula (I) is clothianidin.

5. A method according to claim 1, characterized in that the compound of the formula (I) is nitenpyram.

6. A method according to claim 1, characterized in that the compound of the formula (I) is thiacloporid.

7. A method according to claim 1, characterized in that the compound of the formula (I) is acetamiprid.

8. A method according to claim 1, characterized in that the compound of the formula (I) is MTI-446.

* * * * *

UNITED STATES PATENT AND TRADEMARK OFFICE
CERTIFICATE OF CORRECTION

PATENT NO. : 6,753,296 B1
DATED : June 22, 2004
INVENTOR(S) : Senn et al.

It is certified that error appears in the above-identified patent and that said Letters Patent is hereby corrected as shown below:

Column 9,
Line 31, please insert "Y" prior to "is"

Column 10,
Line 28, please delete "thiacloporid" and insert -- thiacloprid --

Signed and Sealed this

Twenty-third Day of November, 2004

JON W. DUDAS
*Director of the United States Patent and Trademark Office*